United States Patent [19]
Gjerde et al.

[11] Patent Number: 5,772,889
[45] Date of Patent: Jun. 30, 1998

[54] SYSTEM AND METHOD FOR PERFORMING NUCLEIC ACID SEPARATIONS USING LIQUID CHROMATOGRAPHY

[75] Inventors: Douglas T. Gjerde, Saratoga; Robert M. Haefele, Palo Alto; David W. Togami, San Jose, all of Calif.

[73] Assignee: Transgenomic, Inc., San Jose, Calif.

[21] Appl. No.: 748,376

[22] Filed: Nov. 13, 1996

Related U.S. Application Data

[60] Provisional application No. 60/006,477 Nov. 13, 1995.

[51] Int. Cl.⁶ ..................................................... B01D 15/08
[52] U.S. Cl. .......................... 210/635; 210/656; 210/659; 435/6; 536/23.1; 935/18; 935/77
[58] Field of Search ................................ 435/6; 536/23.1; 935/77, 78, 18; 210/635, 656, 659, 198.2

[56] References Cited

U.S. PATENT DOCUMENTS

| | | | |
|---|---|---|---|
| 4,563,510 | 1/1986 | Ugelstad | 562/66 |
| 4,683,202 | 7/1987 | Mullis | 435/91 |
| 4,855,225 | 8/1989 | Fung et al. | 435/6 |
| 5,338,448 | 8/1994 | Gjerde | 210/198.2 |
| 5,585,236 | 12/1996 | Bonn | 435/5 |

FOREIGN PATENT DOCUMENTS

| | | | |
|---|---|---|---|
| 0 507 591 A2 | 10/1992 | European Pat. Off. | 210/656 |
| 94/11305 | 5/1994 | WIPO | 210/656 |

OTHER PUBLICATIONS

J. W. Goodwin et al., Colloid & Polymer Sci., 252:464–471 (1974).
J. Hirabayashi et al., Anal. Biochem., 178:336–341 (1989).
J. Hirabayashi et al., Biochemistry, 29:9515–9521 (1990).
Huber et al., Chomatographia, 37:653–658 (1993).
Y. Kato et al., J. Chromatogr., 478:264–268 (1989).
Y. Ohimya et al., Anal. Biochem., 189:126–130 (1990).
R. K. Saiki et al., Science, 230:1350–1354 (1985).
J. Ugelstad et al., Adv. Colloid Interface Sci., 13:101–140 (1980).
All–Chrom Newsletter, 25:1–6 (Jun. 1986).

*Primary Examiner*—Ernest G. Therkorn
*Attorney, Agent, or Firm*—William B. Walker

[57] ABSTRACT

Improved liquid chromatography systems having components made of titanium, coated stainless steel, or organic polymeric material are useful in the separation of nucleic acid fragments, particularly large fragments of double-stranded nucleic acids, by ion pairing reverse phase chromatography. The titanium, coated stainless steel, or polymeric components do not release multivalent cations into aqueous solutions flowing through the chromatography system. Alternatively, or in addition to utilizing materials made of the components listed above, a multivalent cation capture resin placed upstream of the separation column may be employed to remove multivalent ions from the system. The multivalent cation capture resin may be contained in a guard disk, a guard column, or a guard cartridge. Novel methods for separating mixtures of nucleic acid fragments into fractions based on their molecular weight by ion pairing reverse phase chromatography and slalom chromatography utilize the liquid chromatographic systems described above.

15 Claims, 4 Drawing Sheets

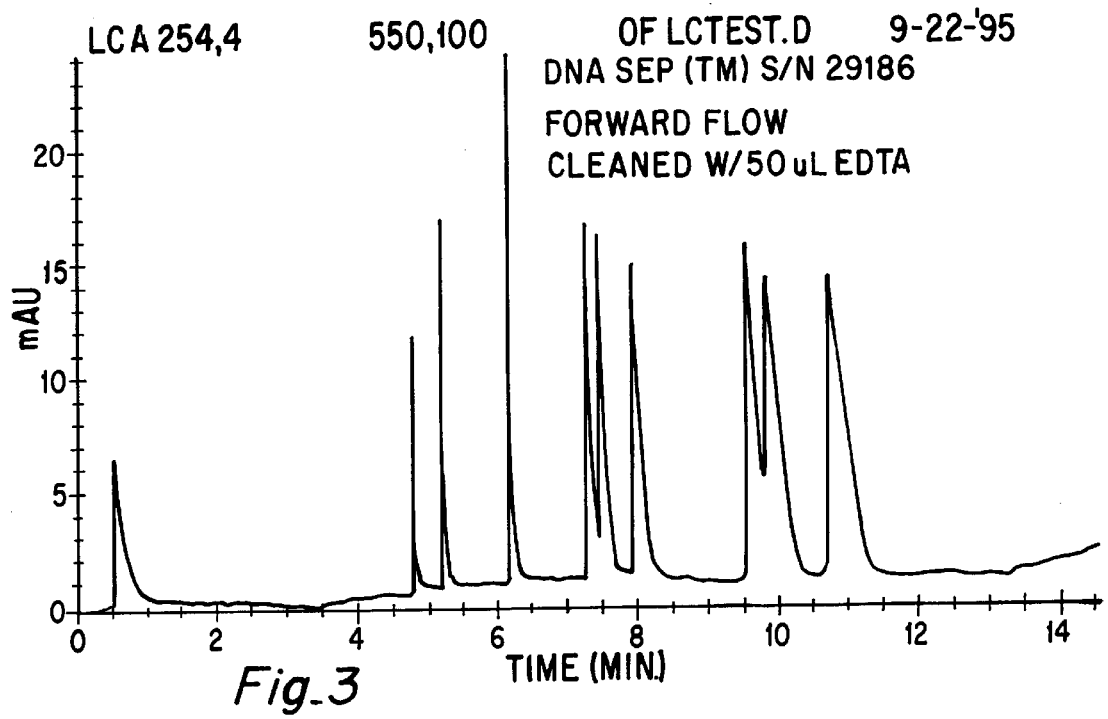
Fig_3
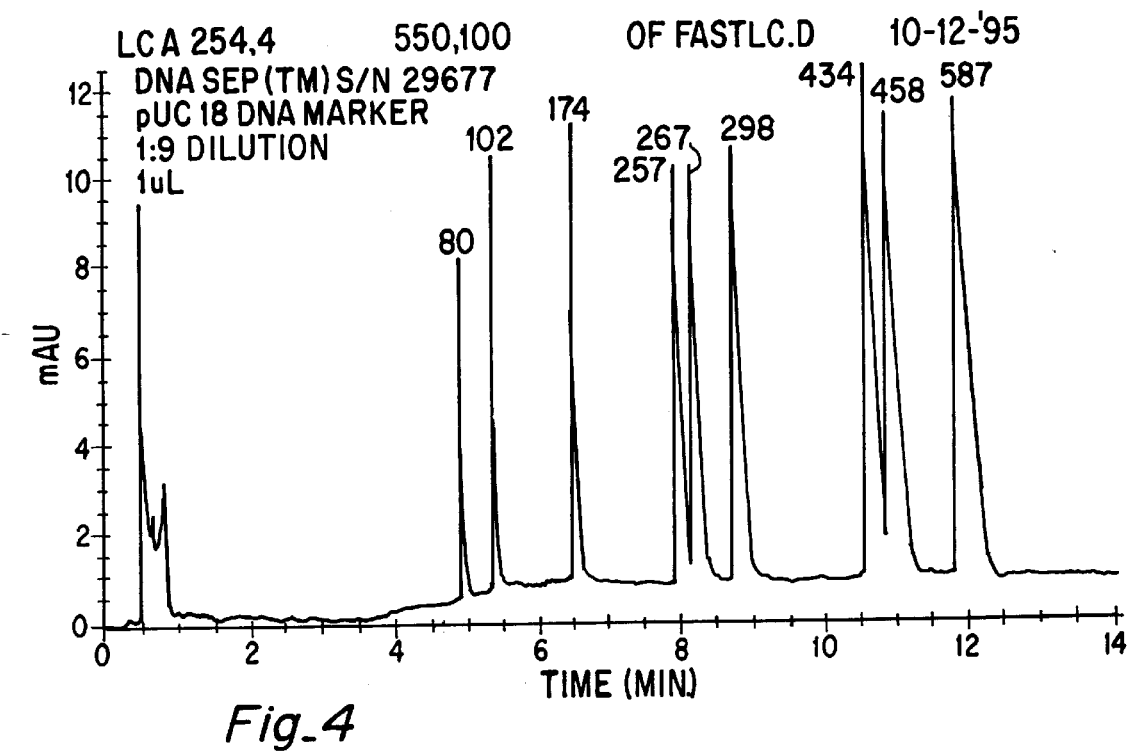
Fig_4

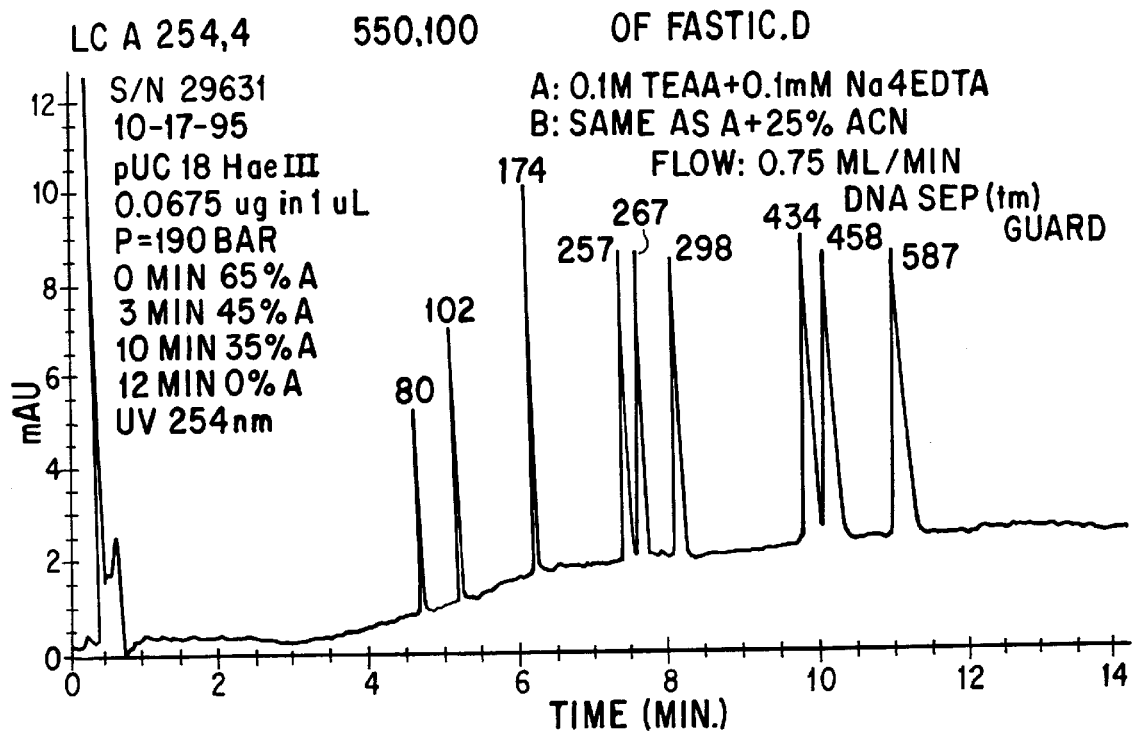
Fig_5
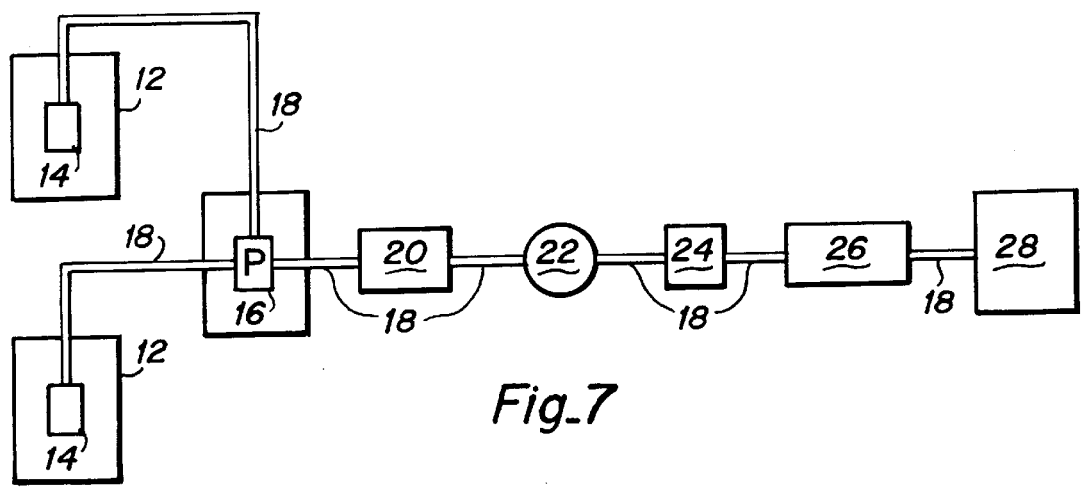
Fig_7

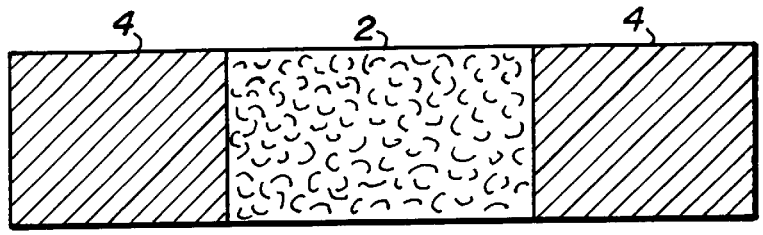
Fig_6A
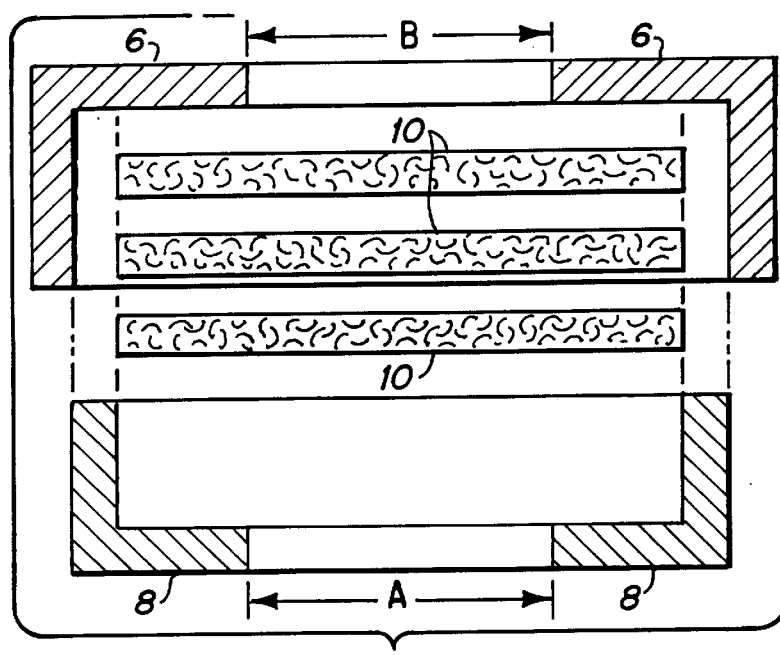
Fig_6B
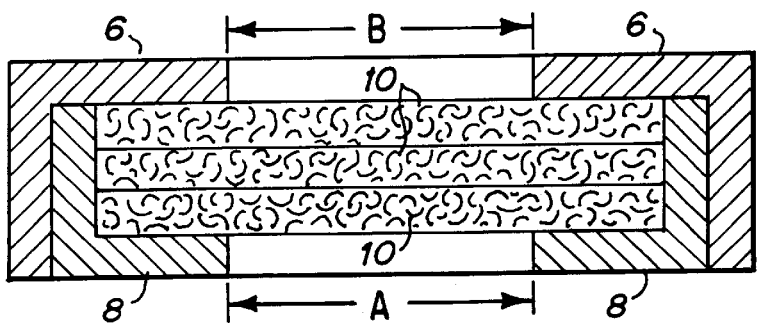
Fig_6C
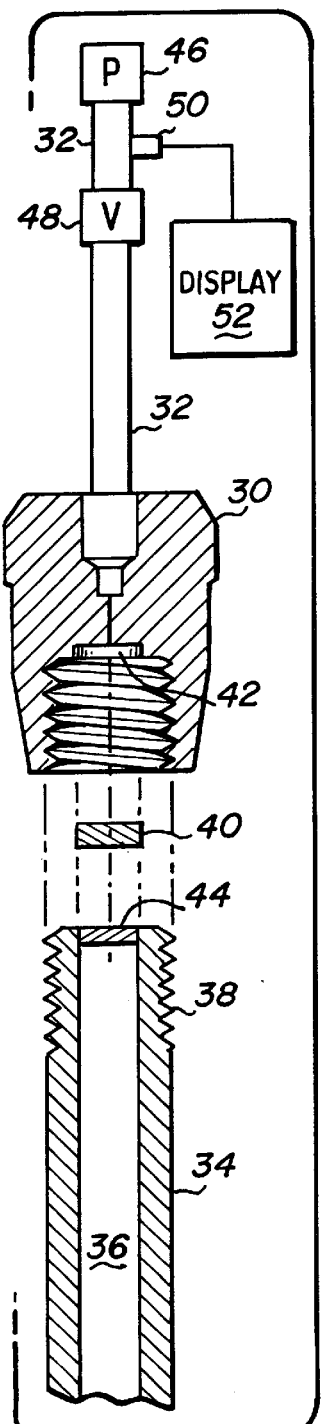
Fig_8

5,772,889

SYSTEM AND METHOD FOR PERFORMING NUCLEIC ACID SEPARATIONS USING LIQUID CHROMATOGRAPHY

CROSS-REFERENCE TO RELATED APPLICATIONS

This application claims the priority of provisional application No. 60/006,477 filed Nov. 13, 1995.

FIELD OF THE INVENTION

The present invention is directed to the separation of nucleic acid fragments by liquid chromatography. More specifically, the invention is directed to a liquid chromatography system and method, such as ion pairing reverse phase chromatography or slalom chromatography, which enhances the separation of nucleic acids.

BACKGROUND OF THE INVENTION

Separation of nucleic acids is a focus of scientific interest, and numerous researchers have been attempting to achieve technical improvements in various aspects of nucleic acid separation. Anion exchange separation and ion pairing reverse phase chromatography are among the most frequently used methods for separating nucleic acids.

Previous work has focused on developing rapid, high resolution separations, developing separations based on the size of the nucleic acid fragment rather than the base sequence of the fragment, and on developing the ability to collect fractions of nucleic acids. W. Bloch (European patent publication No. EP 0 507 591 A2) demonstrated that, to a certain extent, length-relevant separation of nucleic acid fragments was possible on non-porous anion exchangers with tetramethylammonium chloride (TMAC) containing eluants. Y. Ohimya et al. (*Anal. Biochem.*, 189:126–130 (1990)) disclosed a method for separating nucleic acid fragments on anion exchange material carrying trimethylammonium groups. Anion exchangers with diethylaminoethyl groups were used by Y. Kato et al. to separate nucleic acid fragments (*J. Chromatogr.*, 478:264 (1989)).

Although this work is important, anion exchange methods suffer the drawback of differing retention behavior of GC- and AT-base pairs. This effect makes separation according to molecular size impossible. Another important drawback of the anion exchange methodology Is the necessity to use salts and buffers for elution, thus making subsequent investigation of the nucleic acid molecule fractions very difficult.

Bonn et al. (PCT publication WO 9411305) describe a method for separating nucleic acids with ion pairing reverse phase chromatography (IPRPC) utilizing columns filled with nonporous polymeric beads. High resolution, rapid separations were achieved using an ion-pairing reagent, triethylammonium acetate, and acetonitrile/water reagent eluant gradient. This work is important because it is the first separation to give size-dependent, sequence-independent separation of double-stranded nucleic acids by chromatography. These separations are comparable to gel electrophoresis-compatible separations, currently the most widely used technology for nucleic acid separations. Bonn's work makes it possible to automate size-dependent nucleic acid separations.

In the course of our work on separation of nucleic acids using the method developed by Bonn et al., with HPLC instrumentation and columns as described by Bonn, we discovered a degradation effect on the separation of double-stranded nucleic acids after long-term column usage (i.e., greater than about 50 injections). This degradation effect has been generally observed as a loss of resolution for base pairs greater than 200, as illustrated in the chromatogram of FIG. 1. As the degradation worsens, increasingly short fragments of nucleic acids are affected, as shown in FIG. 2. Eventually, the nucleic acids do not elute from the system. As such, the degradation effect or decreasing resolution appears to be a function of the length of the nucleic acid fragment being separated.

There is no published chemical mechanism that would distinguish between different size fragments. Therefore, we first examined our procedure for packing the column. We realized that the molecules that we were attempting to separate were several magnitudes larger in size than those conventionally separated by ion pairing reverse phase liquid chromatography. We suspected that hydrodynamic flow through the column was adequate for short nucleic acid fragments, but was being disrupted for larger fragments. However, we were unable to identify a packing procedure that would discriminate between short and long fragments of nucleic acids.

Although we could not conceive a mechanism by which chemical contamination could produce these unusual results, we nevertheless examined contamination of one or more of the various "pure" reagents employed in liquid chromatography. After testing each of the reagents for contamination, we determined that this was not the source of the problem. This is not surprising, since the eluants used in ion pairing reverse phase liquid chromatography are not corrosive.

Subsequent clean-up of the column with injections of tetrasodium EDTA, a metal-chelating agent, largely restored chromatographic resolution, as shown in FIG. 3. Putting a chelating additive into the mobile phase may provide some protection to the column. We were successful in adding small amounts (i.e., 0.1 mM) of tetrasodium EDTA to the eluant without significant changes to the chromatography. However, this concentration of EDTA was not sufficient to protect the columns in all of the stainless steel HPLC instruments that were tested.

We tested the use of larger amounts of chelator additive in the eluant and found that addition of 10 mM of tetrasodium EDTA impaired the separation of nucleic acids. It was still uncertain that this higher concentration of chelating agent provided an acceptable protective benefit. While use of EDTA injected into the mobile phase (via the HPLC sample injection valve) demonstrated that the column can be regenerated, addition of chelating agents to the mobile phase is not a solution to the problem, as it may hamper use of mass spectrometry detection or fraction collection of the nucleic acid fragments.

We subsequently discovered that placing a cation exchange resin in the flow path of the eluant removed the problem. Guard disks were prepared containing a gel-type iminodiacetate resin with an ion exchange capacity of 2.5 mequiv/g (tested with Cu(II)). FIG. 4 shows a chromatogram obtained when the guard disk was positioned directly in front of the sample injection valve. FIG. 5 shows a chromatogram obtained when the guard disk was placed directly in front of the separation column (i.e., between the injection valve and the column). Attempts to separate nucleic acids on the stainless steel HPLC system without the use of guard disks or guard columns containing cation exchange resin or chelating resin resulted in rapid deterioration of the chromatographic separation.

From the improved results obtained by placing a cation exchange resin in the flow path of the eluant, we concluded that whatever was causing the peak distortion, probably ionic contaminants, was capable of binding to the cation exchange resin. Whatever was causing the fragment size-dependent distortion of the peaks had been removed by the cation exchange resin.

Ionic contamination of the system may logically originate in one or more of several sources. The most significant sources of soluble metal ions are HPLC components containing fritted filters made of stainless steel. Fritted filter components are used in mobile phase filters, check valve filters, helium spargers, eluant mixers, in-line filters, column frits, and other parts of the HPLC. Frits are commonly located at each end of a separation column in order to contain the particulate packing material within the column. The frit at the head of a column also serves to trap particulate material. The large surface area associated with any particular fritted component may contribute to faster solubilization of metals.

In addition to soluble metals, other potential sources of interfering ions exist. For example, colloidal iron may be present, even in "high purity" 18 megohm water. Any metal or other ion that can interact with nucleic acids in the manner described could cause potentially harmful chromatographic effects when the metal becomes trapped on the chromatographic column. Magnesium and/or calcium and other ions may be present in samples such as PCR products. However, at the concentrations typically used, magnesium ions present in PCR products do not harm the peak separation.

In order to test our hypothesis that soluble metals and, potentially, other ions were causing loss of peak resolution during nucleic acid separations, we challenged the HPLC system with iron, chromium, and nickel. Known concentrations of these three metal ions were added to a nucleic acid standard (pUC18 HAE III 0.4 $\mu g/\mu l$). The nucleic acid/metal ion solutions were then injected into the HPLC.

Chromium (III) ions (prepared from $CrK(SO_4)_2$ did not degrade the separation when present in the sample at 9 $\mu M$. However, the sample contained 100 $\mu M$ EDTA as a preservative against enzymatic degradation during storage, and much of the chromium may have been bound in an EDTA complex. However, when chromium was present at 90 $\mu M$, fragment size-dependent degradation of peaks occurred. At 900 $\mu M$ chromium, no peaks could be detected. Several hours later, a sample containing 50 $\mu M$ Cr(III) showed complete loss of the separation peaks.

The same protocol using Ni(II) (prepared from $NiSO_4$) showed substantially no effect on peak shape, although some peak broadening was observed at 0.1M Ni(II).

With Fe(III) (prepared from $FeNH_4(SO_4)_2$), the effect was less than with Cr(III). An injection of 900 $\mu M$ of Fe(III) in the nucleic acid standard showed no effect. However, an injection of 2700 $\mu M$ resulted in a loss of all peaks. There was some indication that the results were time-dependent, with the full effect becoming apparent several minutes after preparation of the metal/nucleic acid sample.

The contact times and metal concentrations of the experiments described above were several orders of magnitude higher than would be found in a stainless steel HPLC system used for nucleic acid separations. Also, none of the experiments indicated how any reaction could be dependent on the size of the nucleic acid fragment. However, these data may show the relative effect separations of some of the metals found in stainless steel on nucleic acid separation.

The effect of metals on the separation of nucleic acids or an effect that discriminated according to fragment size has not been reported in the literature. There are, in fact, only a limited number of publications on the chromatographic separation of nucleic acids; most of these focus on single-stranded nucleic acids. Separation of single-stranded nucleic acids has been performed routinely by many workers, but this is usually on very short lengths of nucleic acid fragments (usually less than 100 mer, with 25 mer the average length), where, based on our observations of double-stranded nucleic acids, we would expect the degradation effect to be much less pronounced.

Gunther Bonn and his colleagues have developed the world's leading chromatographic method for separating double-stranded nucleic acids. Bonn's work was performed on a stainless steel HPLC system with stainless steel hardware, including stainless steel frits. Based on our discovery, we concluded that metal contamination of nucleic acid separations was never reported by Bonn or others because the amount of dissolved and particulate metals in their stainless steel systems was below the threshold where degradation of the separation occurs and the systems worked adequately to produce good peak separations.

Metal-free or titanium instrumentation is commonly used in protein separations, for reasons peculiar to the art of protein separation. For example, the activity of a protein can be affected if a metal is present. If the protein is intended to be collected and studied, separation is generally performed in a metal-free environment. Also, protein separations use particular eluants that can be corrosive to stainless steel HPLC equipment.

Although metal-free or titanium systems are generally used in the separation of proteins for the reasons discussed above, it has been demonstrated that the use of metal-free or titanium systems is not necessary to maintain the integrity of the separation and that stainless steel HPLC systems show equivalent performance (Herold, M. et al., *BioChromatography*, 10:656–662 (1991)). In fact, Hewlett-Packard, one of the leading manufacturers of HPLC systems, now recommends stainless steel systems for use in protein separations.

Because of the success of using stainless steel components in protein separations, and because the use of stainless steel systems for nucleic acid separations had been shown to be successful in the past, there had previously been no indication of the requirement to use non-metal or titanium system components for liquid chromatographic separation of nucleic acid fragments.

SUMMARY OF THE INVENTION

It is an object of the present invention to achieve optimum peak separations during the separation of nucleic acids (particularly double-stranded nucleic acids and, more particularly, large fragments of double-stranded nucleic acids) using ion pairing reverse phase chromatography or slalom chromatography.

It is another object of the invention to extend the maximum useful life of a chromatographic separation column by protecting the column from the potentially deleterious effects of ionic contaminants present within the liquid chromatography system.

The invention is a system and method for separating nucleic acid fragments whereby the effects of metal contamination are avoided. Although the exact mechanism of the degradation effect remains unknown, we have determined that, by avoiding stainless steel or other metal components that may react with phosphate and/or nitrogen groups or unknown groups of the nucleic acids, we are able to separate nucleic acid fragments. This is accomplished by any combination of several measures:

Use of non-metal or titanium frits in the column;
Use of non-metal or titanium frits in the HPLC system;
Use of an ion-binding material upstream of the sample injection valve and/or separation column;
Use of non-metal or titanium system components (e.g., pump heads, tubing, pulse dampeners) anywhere within the system that eluant comes in contact with a surface;
Use of an eluant additive that can capture or bind metals or other ions.

The present invention discloses improved ion pairing reverse phase liquid chromatography systems for separating a mixture of nucleic acid fragments into fractions based on their molecular weight. In one embodiment, the system comprises a chromatographic column containing a separation bed of ion pairing reverse phase (IPRPC) DNA separation resin particles held in the column between porous frits positioned at each end of the column. The column has an inlet, an injection valve which is in communication with the inlet by means of a flow path, and eluant supply means which is (are) in communication with the injection valve by means of at least one flow path. Multivalent cation capture resin capable of removing multivalent cations from aqueous solutions is positioned in the flow path. Using the system of the invention, any multivalent cation contaminants in the flow path are removed before they contact the separation bed.

The multivalent cation capture resin may be cation exchange resin or chelating resin, but is preferably cation exchange resin having an ion exchange moiety selected from the group consisting of iminodiacetate, nitriloacetate, acetylacetone, arsenazo, hydroxypyridinone, and 8-hydroxyquinoline groups. Cation exchange resin having an iminodiacetate group is particularly preferred.

The multivalent cation capture resin is preferably contained in a guard disk, guard column, or guard, and is preferably positioned in the flow path between the eluant supply means and the injection valve. The system further may also include multivalent cation capture resin (preferably contained in a guard disk) positioned in the flow path between the injection valve and the separation column.

The components of the system have process solution-contacting surfaces which contact process solutions held within the component or flowing through the component. The process solution-contacting surfaces are preferably material which does not release multivalent cations; most preferably titanium, coated stainless steel, or organic polymer.

In another embodiment, the system comprises a chromatographic column containing a separation bed of IPRPC DNA separation particles held in the column between porous frits positioned at each end of the column. The column has an inlet, an injection valve which is in communication with the inlet by means of a conduit, and eluant supply means which is (are) in communication with the injection valve by means of at least one conduit. The frits have process solution-contacting surfaces which are made of material which does not release multivalent cations into aqueous solutions flowing through the frits. The material is preferably titanium, coated stainless steel, or organic polymer.

The process solution-contacting surfaces of other system components (such as the chromatographic column, injection valve, eluant supply means, and conduits) are also preferably material which does not release multivalent cations. The system also preferably includes multivalent cation capture resin positioned between the eluant supply means and the injection valve. The multivalent capture resin is preferably cation exchange resin or chelating resin, which is preferably contained in a guard column or guard cartridge. The system may also include multivalent cation capture resin, preferably contained in a guard disk, positioned between the injection valve and the separation column.

Also disclosed herein are methods for improving the separation of nucleic acid fragments into fractions based on their molecular weight during ion pairing reverse phase chromatography using a liquid chromatographic column containing a resin bed comprising IPRPC DNA separation particles. One method comprises supplying and feeding solutions entering the liquid chromatographic separation column with components having process solution-contacting surfaces which are made of material which does not release multivalent cations into aqueous solutions held therein or flowing through the column. The process solution-contacting surfaces of the components are preferably titanium, coated stainless steel, or organic polymer. The IPRPC DNA separation particles particles are preferably alkylated non-porous polymer beads having an average diameter of about 1–100 microns.

The method may further include contacting eluant solutions and sample solutions entering the column with multivalent cation capture resin before the solutions enter the column to protect the resin bed from multivalent cation contamination. The method is preferably used for separating double-stranded nucleic acid fragments, particularly those having 80 or more base pairs.

In an alternative method for improving the separation of nucleic acid fragments into fractions based on their molecular weight during ion pairing reverse phase chromatography using a liquid chromatographic column containing a resin bed comprising IPRPC DNA separation particles, process solutions are contacted with multivalent cation capture resin before the solutions enter the chromatographic column in order to protect the resin bed from multivalent cation contamination. The multivalent cation capture resin may be cation exchange resin or chelating resin, but is preferably a cation exchange resin having an ion exchange moiety selected from the group consisting of iminodiacetate, nitriloacetate, acetylacetone, arsenazo, hydroxypyridinone, and 8-hydroxyquinoline groups. Cation exchange resin having an iminodiacetate group is particularly preferred. The multivalent cation capture resin is preferably contained in a guard disk, guard column, or guard cartridge. The IPRPC DNA separation particles particles are preferably alkylated non-porous polymer beads having an average diameter of about 1–100 microns.

The method may further include supplying and feeding solutions entering the column with components having process solution-contacting surfaces which are material which does not release multivalent cations into process solutions so that the contents of the column are protected from multivalent cation contamination. The process solution-contacting surfaces of the components are preferably titanium, coated stainless steel, or organic polymer. The method is preferably used for separating double-stranded nucleic acid fragments, particularly those having 80 or more base pairs.

Also disclosed herein is method for improving separation of nucleic acid fragments into fractions based on their molecular weight weight during slalom chromatography using a liquid chromatographic column containing a resin bed comprising slalom chromatography DNA separation particles. The method comprises contacting the process solutions with multivalent cation capture resin before the solutions enter the chromatographic column in order to protect the resin bed from multivalent cation contamination.

The multivalent cation capture resin may be cation exchange resin or chelating resin, but is preferably cation exchange resin having an ion exchange moiety selected from the group consisting of iminodiacetate, nitriloacetate, acetylacetone, arsenazo, hydroxypyridinone, and 8-hydroxyquinoline groups. Cation exchange resin having an iminodiacetate group is particularly preferred. The multivalent cation capture resin is preferably contained in a guard disk, guard column, or guard cartridge.

The method may further include supplying and feeding solutions entering the column with components having process solution-contacting surfaces which are material which does not release multivalent cations into process solutions so that the contents of the column are protected from multivalent cation contamination. The process solution-contacting surfaces of the components are preferably titanium, coated stainless steel, or organic polymer. The method is preferably used for separating double-stranded nucleic acid fragments, particularly those having 5000 or more base pairs.

BRIEF DESCRIPTION OF THE DRAWINGS

FIG. 3 shows a chromatogram of nucleic acid separation following injection of the column with tetrasodium EDTA, a metal chelating agent.

FIG. 4 shows a chromatogram of nucleic acid separation obtained when a guard disk containing gel-type iminodiacetate was positioned directly in front of the sample injection valve of the HPLC system.

FIG. 5 shows a chromatogram of nucleic acid separation obtained when a guard disk containing gel-type iminodiacetate was placed directly in front of the separation column of the HPLC system (i.e., between the sample injection valve and the separation column).

FIG. 6A shows a guard disk having a one-piece annular ring. FIG. 6B is an exploded view of a guard disk having a two-piece annular ring and containing three pads of guard disk material (i.e., a layer or pad of multivalent cation capture resin which has been incorporated into a fabric or membrane). FIG. 6C shows an assembled view of the guard disk of FIG. 6B.

FIG. 7 shows placement of a chelating guard column and chelating guard disk in a liquid chromatographic system for nucleic acid separation.

FIG. 8 shows placement of a chelating guard disk positioned between a chromatographic separation column and a column top, where the guard disk is in direct contact with a titanium frit at the top portion of the separation column.

DETAILED DESCRIPTION OF THE INVENTION

Systems

Figure 1:
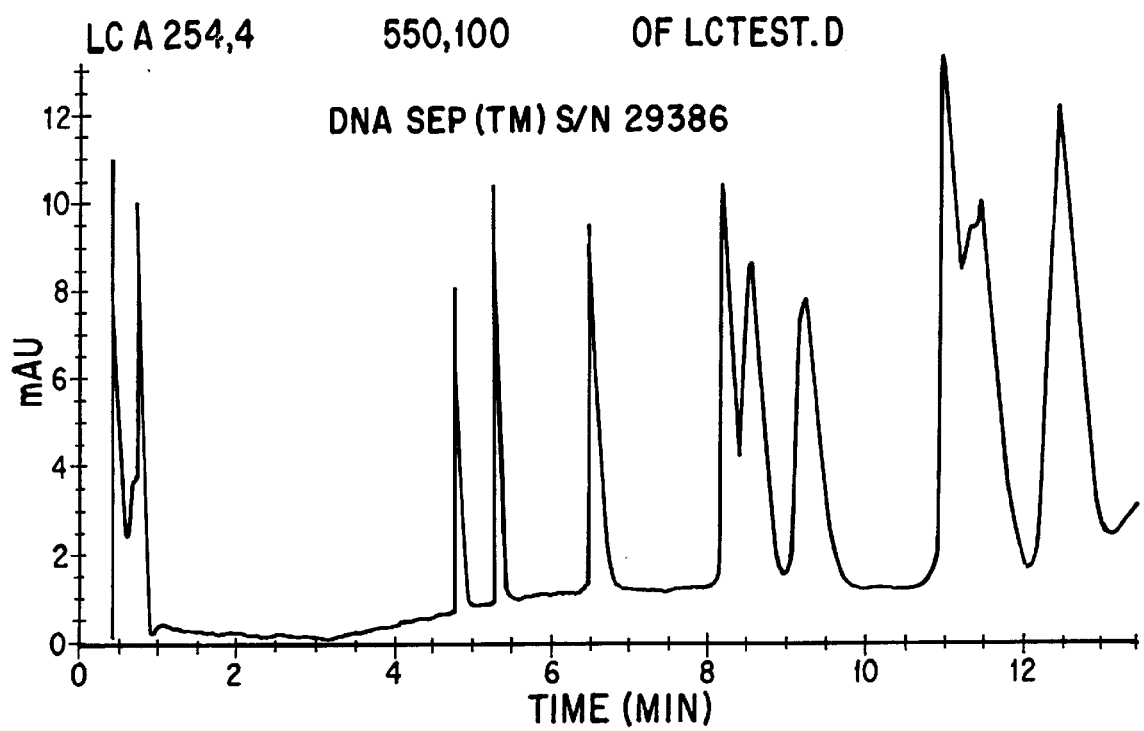
FIG. 1 shows a chromatogram of double-stranded nucleic acid separation illustrating the degradation effect on peak separation caused by ionic contaminants present within the HPLC system. In this case, the degradation effect is greater than about 174 base pairs.

The system of the invention includes a chromatographic column containing a separation bed of IPRPC DNA separation particles held in the column between porous frits positioned at each end of the column.

The term "IPRPC DNA separation particles" refers to any material which is capable of separating nucleic acid fragments by ion pairing reverse phase chromatography ("IPRPC"). The IPRPC DNA separation particles may be inorganic, including silica, zirconium, alumina, or other material, or may be polymeric, including crosslinked resins of polystyrene, polyacrylates, polyethylene, or other organic polymeric material. The only requirement for the IPRPC DNA separation particles is that they must have a surface that is either intrinsically hydrophobic or be bonded with a material that forms a surface having sufficient hydrophobicity to interact with an ion pairing reagent. Preferred IPRPC DNA separation particles are non-porous, or have pores which are sufficiently small as to exclude the particles being separated. A preferred IPRPC DNA separation particles comprises alkylated non-porous polymer beads having an average diameter of about 1–100 microns, which are described in further detail in the "Methods" section below.

Other components of the liquid chromatography system include an injection valve and one or more eluant supply means. Eluant supply means is (are) connected to the injection valve, and the injection valve is connected to the inlet of the chromatographic separation column, by means of conduit (e.g., tubing), as illustrated in FIG. 8.

The components of the liquid chromatography system have surfaces (i.e., "process solution-contacting surfaces") which contact process solutions held within the component (e.g., the eluant supply means) or flowing through the component (e.g., the porous frits, chromatographic column, injection valve, and conduits). The term "process solution" as used herein refers to any solution (such as a sample solution or eluant solution) which is contained within or flows through any component of the liquid chromatography system during liquid chromatography. The term "process solution-contacting surface" refers to any surface of a liquid chromatography system to which process solutions are exposed during performance of chromatographic separations.

The process solution-contacting surfaces of the porous frits on either end of the separation column must be made of material which does not release multivalent cations into aqueous solutions flowing through the column. The material is preferably titanium, coated stainless steel, or organic polymer, but is most preferably titanium. The term "coated stainless steel" as used herein refers to stainless steel that has been coated with a hydrophobic material that does not release multivalent cations, such as polytetrafluoroethylene (i.e., Teflon®).

Other components of the liquid chromatography system are also preferably titanium, coated stainless steel, or organic polymer, such as poly ether ether ketone (PEEK) or polyethylene. The preferred system tubing (i.e., conduit) is titanium, PEEK, or other polymeric material, with an inner diameter of 0.007". The preferred eluant inlet filters are composed of a non-stainless steel porous material, which may be PEEK, polyethylene, or other polymeric material. The preferred solvent pump is also made of a non-stainless steel material; the pump heads, check valves, and solvent filters are preferably titanium, PEEK, or other polymeric material. The sample injection valve is also preferably titanium, PEEK, or other polymeric material. A standard detector and eluant reservoirs may be used, with no modifications necessary.

As an alternative to using the system described above, a stainless steel HPLC system can be used if a component for removing multivalent cations, herein referred to as a "multivalent cation capture resin", is also used. A multivalent cation capture resin is preferably a cation exchange resin or chelating resin. Any suitable cation exchange resin or chelating resin may be used. Preferred cation exchange and chelating resins are described below.

Cation exchange resins having an ion exchange moiety selected from the group consisting of iminodiacetate, nitriloacetate, acetylacetone, arsenazo, hydroxypyridinone, and 8-hydroxyquinoline groups are particularly preferred. Cation exchange resins having hydroxypyridinone groups are especially useful for removing iron from the system. Cation exchange resins having iminodiacetate groups are particularly preferred for use in the present invention because of their wide availability in resin format.

A chelating (i.e., coordination binding) resin is an organic compound which is capable of forming more than one non-covalent bond with a metal. Chelating resins include tetrasodium EDTA and crown ethers. Crown ethers are cyclic oligomers of ethylene oxide which are able to interact strongly with alkali or alkaline earth cations. A cavity in the center of the molecule is lined with oxygen atoms which hold cations by electrostatic attraction. Each ether has a strong preference for cations whose ionic radius best fits the cavity.

The multivalent cation capture resin is preferably contained in a guard column, guard cartridge, or guard disk. Guard columns and cartridges are frequently used to protect liquid chromatography columns from contamination and are widely available. In their normal use, guard columns and cartridges typically contain packing material which is similar to the stationary phase of the separation column. However, for use in the present invention, the guard column or cartridge must contain a multivalent cation capture resin.

For use in the system of the present invention, the guard cartridge or column should be sufficiently large to provide adequate capacity, but must be small enough to allow effective gradient elution to be used. A preferred guard cartridge has a void volume of less than 5 milliliters, more preferably, less than 1 milliliter, so that the eluant gradient is not delayed by more than 5 minutes and, preferably, less than 1 minute. The preferred cartridge has a 10×3.2 millimeter bed volume.

Guard disks are described in detail in U.S. Pat. No. 5,338,448, which is incorporated herein by reference in its entirety. For use in the present invention, a guard disk comprises a layer or pad of a multivalent cation capture resin which has been incorporated into a fabric or membrane so that the resin is not separable from the guard disk under liquid flow conditions present during the performance of chromatographic separations.

In its preferred form, the guard disk is circular, having a rigid annular outer ring or collar for easy handling. The annular ring may be constructed of any suitable material which is inert to the chromatographic separation, such as inert conventional engineering plastic. The only requirement for the material is that it must be inert to the eluate solvent and sample and have sufficient dimensional stability. The rigid annular outer ring of the guard disk may comprise a single rigid annular outer ring encircling a disk-shaped pad of guard disk material. As used herein, the term "guard disk material" refers to a layer or pad of multivalent cation capture resin which has been incorporated into a fabric or membrane.

As shown in FIG. 6A, one or more pads of guard disk material 2 are placed in the rigid annular ring 4. For example, the fabric may be cut to a circular diameter which securely contacts the inner diameter surface of the annular ring. As the disk holder is tightened against the disk, the top and bottom surfaces of the holder seal against the collar of the guard disk. Sealing pressure from the guard disk holder is, therefore, applied against the collar of the disk which prevents the material of the guard disk pad from being crushed.

Alternatively, the rigid annular outer ring may comprise two flanged rings, as shown in FIGS. 6B and 6C, an outer flanged ring 6 and an inner flanged ring 8, where the inner flanged ring is insertable within the flange of the outer ring, forming a press-fit two-piece collar around one or more pads of guard disk material 10. Preferably, the inner diameter (a) of the inner flanged ring will have the same diameter as the separation column bed.

In the two-piece annular ring embodiment shown in FIG. 6C, one or more pads of guard disk material 10 having a diameter greater than the inner diameter (b) of the outer flanged ring 6 are positioned within the flanges of the outer ring. The inner flanged ring 8 is then inserted into the outer ring to form a press-fit two-piece annular ring in which the guard disk pad(s) is (are) frictionally held within the press-fit ring or collar. Preferably, the inner diameter (b) of the outer flanged ring and the inner diameter (a) of the inner flanged ring are substantially the same.

Alternatively, the rigid annular outer ring may be incorporated into the guard disk holder or chromatographic column cap. The annular ring is a flange that is part of one or both sides of the disk holder or the column cap. In this case, the guard disk does not have an outer ring. A circle of the guard disk sheet material is placed into the holder or column cap. The flange in the holder column cap is annular so that, when the holder or column cap is tightened, the flange pinches or seals the outer annular portion of the guard disk. The center portion of the guard disk not pinched is in a chamber or depression in the holder or cap. Fluid flows through the center portion, allowing the guard disk to retain particulate or strongly adsorbed material, but fluid cannot flow around the disk or past the edges. The function of the guard disk is exactly the same as when the collar is part of the guard disk itself. However, in this case, the collar is part of the holder or column cap.

In the system of the invention, a multivalent cation capture resin contained in a guard column, guard cartridge, or guard disk is placed upstream of the separation column. Preferably, the guard column, cartridge, or disk containing the resin is placed upstream of the sample injection valve. Although this is preferably a guard disk, a guard cartridge or column may be used as long as the dead volume of the cartridge or column is not excessive and an effective eluant gradient can be produced.

Additionally, a second guard disk, column, or cartridge can be placed between the sample injection valve and the separation column. In certain cases, the second guard disk (or cartridge or column) can be avoided if the contaminants are sufficiently cleaned by a guard column placed upstream of the injection valve, or if the contaminants are avoided through the use of non-metal or titanium components throughout the HPLC system.

Placement of a chelating guard column and chelating guard disk in a liquid chromatography system for nucleic acid separation is illustrated in FIG. 7. The eluant reservoirs 12 contain eluant inlet filters 14 which are connected to the solvent pump 16 by system tubing 18. The solvent pump 16 is connected to a chelating column 20 by system tubing 18. The chelating column 20 is connected to the sample injection valve 22 by system tubing 18. The sample injection valve has means for injecting a sample (not shown). The sample injection valve 22 is connected to a chelating guard disk 24 by system tubing 18. The chelating guard disk 24 is connected to the inlet (not shown) of the separation column 26 by system tubing 18. Detector 28 is connected to the separation column 26. As discussed above, the system tubing, eluant inlet filters, solvent pump, sample injection valve, and separation column are preferably made of titanium, coated stainless steel, or organic polymer.

In operation, eluant from the eluant reservoirs 12 is pumped through eluant inlet filters 14 by solvent pump 16. By way of system tubing 18, the eluant stream flows through chelating column 20, through sample injection valve 22, through chelating guard disk 24, then into separation column 26. Detector 28 is located downstream from separation column 26.

FIG. 8 illustrates a specific embodiment of the invention in which a chelating guard disk is placed in direct contact with a titanium frit at the top portion of a chromatographic separation column. Column top 30 has conventional fittings for receiving eluate solvent and sample through inlet tubing 32. The column top or cap 30 is fitted and sealably attached to column body 34 containing chromatographic bed 36 using a conventional fitting 38 (e.g., threaded) or any equivalent fitting capable of tightly sealing the column top to the column body. The column top 30 is adapted to receive the chelating guard disk 40 in a sealing cavity 42. In this embodiment, the guard disk 40 is in direct contact with a titanium column frit 44, which is located at the upstream end of the column body 34 to prevent disturbance of the chromatographic bed 36 when the column top 30 is removed to observe the guard disk.

In operation, solvent pump 46 pumps elution solvent to sample injection valve 48 into column top 30 through chelating guard disk 40 and then through titanium frit 44 before entering chromatographic bed 36. Eluate pressure upstream from the guard disk is measured by pressure transducer 50 which is electrically connected to a display device 52.

As discussed above, a chelating guard column, cartridge, or disk can be used in conjunction with a conventional, stainless steel liquid chromatography system, or with a system containing non-metal or titanium components in order to provide extra protection against ionic contaminants. For additional column protection, an eluant containing 0.1 mM tetrasodium EDTA or other chelating solution can be used during the performance of nucleic acid separations.

Methods

The methods of the invention comprise using the improved systems described above to separate mixtures of nucleic acid fragments, particularly double-stranded nucleic acid fragments. The methods of the present invention can be used to separate nucleic acid fragments having up to about 1500 base pairs using ion pairing reverse phase liquid chromatography and up to about 20,000 base pairs using slalom chromatography.

In most cases, the method will be used to separate nucleic acids having 80 or more base pairs, up to about 1500 base pairs. The method provides good separation and reliability for longer nucleic acids having base pairs within the range of 10–100, but is also useful for base pairs less than 10.

The nucleic acids which may be separated by the present method include double-stranded nucleic acids. Since the mechanism of the degradation effect is still unknown, it is not known how significantly single-stranded nucleic acid separations are affected. Furthermore, only short (25 mer) single-stranded nucleic acids are usually separated by liquid chromatographic methods. With short lengths, the effect is more difficult to detect.

Samples containing mixtures of nucleic acids may result from total synthesis of nucleic acids, cleavage of DNA or RNA with restriction endonucleases, as well as nucleic acid samples which have been multiplied or amplified using polymerase chain reaction (PCR) techniques or other amplifying techniques.

The systems of the present invention are preferably used to separate double-stranded nucleic acid fragments according to the method for ion pairing reverse phase chromatography (IPRPC). The preferred IPRPC method is described by Bonn et al. in PCT publication WO 9411305, which is incorporated herein by reference in its entirety. The method of Bonn et al. utilizes separation columns filled with nonporous polymeric beads having an average diameter of about 1–100 microns, preferably 1–10 microns, more preferably 1–5 microns. Beads having an average diameter of 1.5–3.0 microns are most preferred.

The nonporous polymeric beads are prepared by a two-step process in which small seed beads are initially produced by emulsion polymerization of suitable polymerizable monomers. The emulsion polymerization procedure of the invention is a modification of the procedure of J. W. Goodwin et al. (*Colloid & Polymer Sci.*, 252:464–471 (1974)). Monomers which may be used in the emulsion polymerization process to produce the seed beads include styrene, alkyl substituted styrenes, alpha-methyl styrene, and alkyl substituted alpha-methyl styrenes, preferably monomers where the benzene-type ring is substituted with 1–4 $C_{1-6}$ alkyl groups, and the monomers described, for example, in U.S. Pat. No. 4,563,510. The seed polymer beads are then enlarged and alkylated, as described by Bonn et al. in PCT publication WO 9411305.

In IPRPC, the nucleic acids are paired with an ion-pairing agent and then subjected to reverse phase chromatography using the alkylated beads described above. The identity of the ion-pairing agent is not critical and conventional ion-pairing agents capable of forming ion pairs with nucleic acids may be used. Typical ion-pairing agents include trialkylammonium salts of organic or inorganic acids, for example, trimethyl, triethyl, tripropyl, and tributyl ammonium acetates, halides, etc. A particularly preferred ion-pairing agent is triethylammonium acetate (TEAA).

To achieve high resolution chromatographic separations of nucleic acids, it is generally necessary to tightly pack the chromatographic column with the solid phase polymer beads. Any known method of packing the column with a column packing material may be used to obtain adequate high resolution separations. Typically, a slurry of the alkylated polymer beads is prepared using a solvent having a density equal to or less than the density of the polymer beads. The column is then filled with the polymer bead slurry and vibrated or agitated to improve the packing density of the polymer beads in the column. Mechanical vibration or sonication are typically used to improve packing density.

For example, to pack a column having an inner diameter of 50×4.6 millimeters, 1.4 grams of alkylated beads may be suspended in 15 milliliters of tetrahydrofuran with the help of sonication. The suspension is then packed into the column using 50 milliliters of methanol at 70 MPa of pressure. In the final step, the packed bed is washed with 50 milliliters of deionized water. This reduces the swelling of the beads and improves the density of the packed bed.

Alternatively, slalom chromatography can be used to separate larger nucleic acid fragments (i.e., 5000 or more base pairs) according to the methods of the invention. Slalom chromatography, as described by J. Hirabayashi et al. (*Anal. Biochem.*, 178:336–341 (1989); *Biochemistry*, 29:9515–9521 (1990)), is a method of separating nucleic acid fragments having dimensions comparable to the chromatographic particles. In practice, this means that currently available columns separate fragments in the range of 5000–50,000 base pairs. Fragments are eluted in order of size, with the smallest fragments eluting first, opposite to the order of gel permeation. The mechanism is believed to be hydrodynamic sieving, rather than surface interactions between the nucleic acid and the chromatographic packing. Particle size and eluant flow rate have the greatest influence on separation. While the eluant is usually aqueous buffer, organic or aqueous organic eluants are not excluded.

In slalom chromatography, the chromatographic separation column is packed with "slalom chromatography DNA separation particles". The term "slalom chromatography DNA separation particles" refers to any material which is capable of separating nucleic acid fragments by slalom chromatography. Slalom chromatography separation particles may be inert organic polymers, inert inorganic polymers, silica, or cation exchange resin. The only requirement for the slalom chromatography DNA separation particles is that they must have little interaction with nucleic acids.

EXPERIMENTAL

Example 1

Sodium chloride (0.236 g) was added to 354 ml of deionized water in a reactor having a volume of 1.0 liter. The reactor was equipped with a mechanical stirrer, reflux condenser, and a gas introduction tube. The dissolution of the sodium chloride was carried out under inert atmosphere (argon), assisted by stirring (350 rpm), and at an elevated temperature (87° C.). Freshly distilled styrene (33.7 g) and 0.2184 g of potassium peroxodisulfate ($K_2S_2O_8$) dissolved in 50 ml of deionized water were then added. Immediately after these additions, the gas introduction tube was pulled out of the solution and positioned above the liquid surface. The reaction mixture was subsequently stirred for 6.5 hours at 87° C. After this, the contents of the reactor were cooled down to ambient temperature and diluted to a volume yielding a concentration of 54.6 g of polymerized styrene in 1000 ml volume of suspension resulting from the first step. The amount of polymerized styrene in 1000 ml was calculated to include the quantity of the polymer still sticking to the mechanical stirrer (approximately 5–10 g). The diameter of the spherical beads in the suspension was determined by light microscopy to be about 1.0 micron.

Beads resulting from the first step are still generally too small and too soft (low pressure stability) for use as chromatographic packings. The softness of these beads is caused by an insufficient degree of crosslinking. In a second step, the beads are enlarged and the degree of crosslinking is increased. The protocol for the second step is based on the activated swelling method described by Ugelstad et al. (*Adv. Colloid Interface Sci.*, 13:101–140 (1980)). In order to initiate activated swelling, or the second synthetic step, the aqueous suspension of polystyrene seeds (200 ml) from the first step was mixed first with 60 ml of acetone and then with 60 ml of a 1-chlorododecane emulsion. To prepare the emulsion, 0.206 g of sodium dodecylsulfate, 49.5 ml of deionized water, and 10.5 ml of 1-chlorododecane were brought together and the resulting mixture was kept at 0° C. for 4 hours and mixed by sonication during the entire time period until a fine emulsion of <0.3 microns was obtained. The mixture of polystyrene seeds, acetone, and 1-chlorododecane emulsion was stirred for about 12 hours at room temperature, during which time the swelling of the beads occurred. Subsequently, the acetone was removed by a 30 minute distillation at 80° C. Following the removal of acetone, the swollen beads were further grown by the addition of 310 g of a ethyldivinylbenzene and divinylbenzene (DVB) (1:1.71) mixture also containing 2.5 g of dibenzoylperoxide as an initiator. The growing occurred with stirring and with occasional particle size measurements by means of light microscopy, as described in Example 2.

After completion of the swelling and growing stages, the reaction mixture was transferred into a separation funnel. In an unstirred solution, the excess amount of the monomer separated from the layer containing the suspension of the polymeric beads and could thus be easily removed. The remaining suspension of beads was returned to the reactor and subjected to a stepwise increase in temperature (63° C. for about 7 hours, 73° C. for about 2 hours, and 83° C. for about 12 hours), leading to further increases in the degree of polymerization (>500). The pore size of beads prepared in this manner was below the detection limit of mercury porosimetry (<30A). After drying, the dried beads (10 g) from step two were suspended in 100 ml of 1-chlorododecane and stirred (370 rpm) for 12 hours at 100° C. following addition of 1 g of aluminum chloride. At the end of this period, the reaction mixture was cooled to 80° C. and mixed with 150 ml of 4M hydrochloric acid. After 2 minutes of stirring, the reaction mixture, now containing hydrochloric acid, was transferred into a separation funnel and overlaid by 300 ml of n-heptane. The phases were stirred into each other and, after subsequent separation of phases, the aqueous phase was removed and discarded. The remaining organic phase was washed two additional times with 200 ml of 1M hydrochloric acid and subsequently centrifuged at 5000 rpm. The separated beads were washed four times with 100 ml of n-heptane, and then two times with each of the following: 100 ml of diethylether, 100 ml of dioxane, and 100 ml of methanol. Finally, the beads were dried.

Alternatively, the alkylation was carried out using tin chloride by means of a procedure which is otherwise similar to that utilizing aluminum chloride. One hundred milliliters (100 ml) of 1-chlorooctadecane, 10 g of poly(styrene/ethylstyrene/divinylbenzene) beads, and 5 ml of $SnCl_4$ were stirred at 100° C. for 12 hours. The mixture was cooled to room temperature, 100 ml of n-heptane was added and the mixture was then extracted with 4×300 ml of water in a separation funnel. Subsequent centrifugation was carried out for 5 minutes at 5000 rpm. The supernatant and 1-chlorooctadecane were discarded and water was removed as completely as possible. Washing with 2×150 ml of n-heptane, 2×150 ml of dioxane, and 2×150 ml of methanol completed the procedure. Each of the washing steps was followed by centrifugation at 5000 rpm. The alkylated beads were then dried at 60° C.

Alkylation of the aromatic rings of the polymer was verified by Fourier Transform Infrared spectroscopy (FTIR). The beads differed only slightly in size from each other. The mean value for the particle diameter was found to be 2.10 microns, with a standard deviation of 0.12 micron.

The separation of single- and double-stranded nucleic acids was accomplished using IPRPC. Triethylammonium acetate was used as the ion-pairing agent. Elution was effected with the help of a linear organic solvent gradient of acetonitrile. The chromatographic conditions were as follows: Column: 50×4.6 cm i.d. Mobile phase: 0.1M TEAA, pH 7.0. Gradient: 7.5–13.75% acetonitrile in 4 minutes, followed by 13.75–16.25% acetonitrile in 6 minutes. Flow rate: 1 ml/min. Column temperature: 50° C. Detection: UV at 254 nm. Sample: 0.5 µg pBR322 DNA-Hae III restriction digest.

Example 2

Seed polystyrene latex was prepared using 0.374 g of NaCl, 0.1638 g of $K_2S_2O_8$, 404 ml of water, and 37 ml of styrene, stirred at 81° C. at 350 rpm for 6 hours. The resulting seed particles had a diameter of 1.3 microns. Then, 200 ml of the seed latex was swollen with a mixture of 50 ml of divinylbenzene, 0.5 ml of dibenzoylperoxide, and 5 ml of acetone. The mixture was stirred for 6 hours at 40° C. and 1 hour at 45° C. The final diameter of the particles was 1.8 microns. Next, the excess divinylbenzene was removed and the particles polymerized for 12 hours at 65° C., followed by 14 hours at 85° C. After drying, alkylating, and cleaning, the polymer was used as described in Example 1.

Example 3

Many experiments in molecular biology, including hybridization and DNA sequencing, require tagging of nucleic acids with either radioactive isotopes, such as $^{32}P$ or $^{33}P$ or fluorescent dyes, such as fluorescein, 2',7'-dimethyoxy-4',5'-dichlorofluorescein, tetramethylrhodamine, and rhodoamine, as described by S. Fung et al. (U.S. Pat. No. 4,855,225). Since the coupling of radioisotopes and fluorescent dyes is usually incomplete, labeled nucleic acids must be purified away from unreacted nucleic acids, which otherwise will compete with the dye-labeled primers and probes in sequencing and hybridization reactions.

The purification of labeled samples was accomplished simply and rapidly by means of IPRPC on nonporous, alkylated ($C_{18}$) poly(ethylvinylbenzene-divinylbenzene) beads. Recovery of nucleic acids was at least 96%.

The separation of fluorescent dye-labeled nucleic acids from unreacted nucleic acids can also be achieved by reverse phase chromatography only, i.e., in the absence of an ion-pairing reagent, because the hydrophobic nature of the fluorophore significantly increases their retention on an alkylated stationary phase relative to unreacted nucleic acids.

Example 4

If the gradient delay volume is minimized, the separation of PCR products and hybrid nucleic acids derived from various sources of nucleic acids, including living and dead organisms (animal and plant), as well as parts of such organisms (e.g., blood cells biopsies, sperm, etc.) on octadecyl-modified, nonporous poly-(ethylvinylbenzene-divinylbenzene)beads can be achieved with run times under 2 minutes.

The analysis of PCR products and hybrid nucleic acids usually requires only separation and detection of one or two species of known length. Because of this, the resolution requirements are considerably less severe than for separations of DNA restriction fragments. Such less stringent resolution requirements allow the utilization of steep gradients and, consequently, lead to still shorter run times. The recovery rate for a nucleic acid fragment containing 404 base pairs was about 97.5%.

Unlike capillary electrophoresis (CE), PCR samples do not have to be desalted prior to analysis of IPRPC. This represents a decisive advantage of IPRPC over CE. With IPRPC, it is thus possible to achieve a fully automated analysis of PCR samples if an automatic autosampler is utilized. Moreover, since the volume of sample injection is known, in contrast to CE, quantitation over several orders of magnitude can be achieved without the need for an internal standard, hence allowing the quantitation of gene expression, as well as the determination of virus titers in tissues and body fluids. A fully automated version of the method of the invention has been used to discriminate (i.e., distinguish) normal from mutated genes, as well as to detect oncogenes and bacterial and viral genome nucleic acids (hepatitis C virus, HIV, tuberculosis) for diagnostic purposes. Moreover, adjustment of column temperature allows the stringency of hybridization reactions to be modulated.

PCR methods and processes have been described by R. K. Sreke et al. (Science, 230:1350–1354 (1985)) and K. B. Mullis (U.S. Pat. No. 4,683,202). These references are incorporated herein by reference for a more complete description of methods and processes for obtaining PCR samples which can be separated using the method of the present invention.

Example 5

A Hewlett-Packard HP1090 instrument formerly used for protein separations was purchased and outfitted with a column and eluants as described in Examples 1 and 2. In this case, the column contained 0.5 µm 316 stainless steel frits. The HP1090 instrument is available only as a stainless steel instrument.

Figure 2:
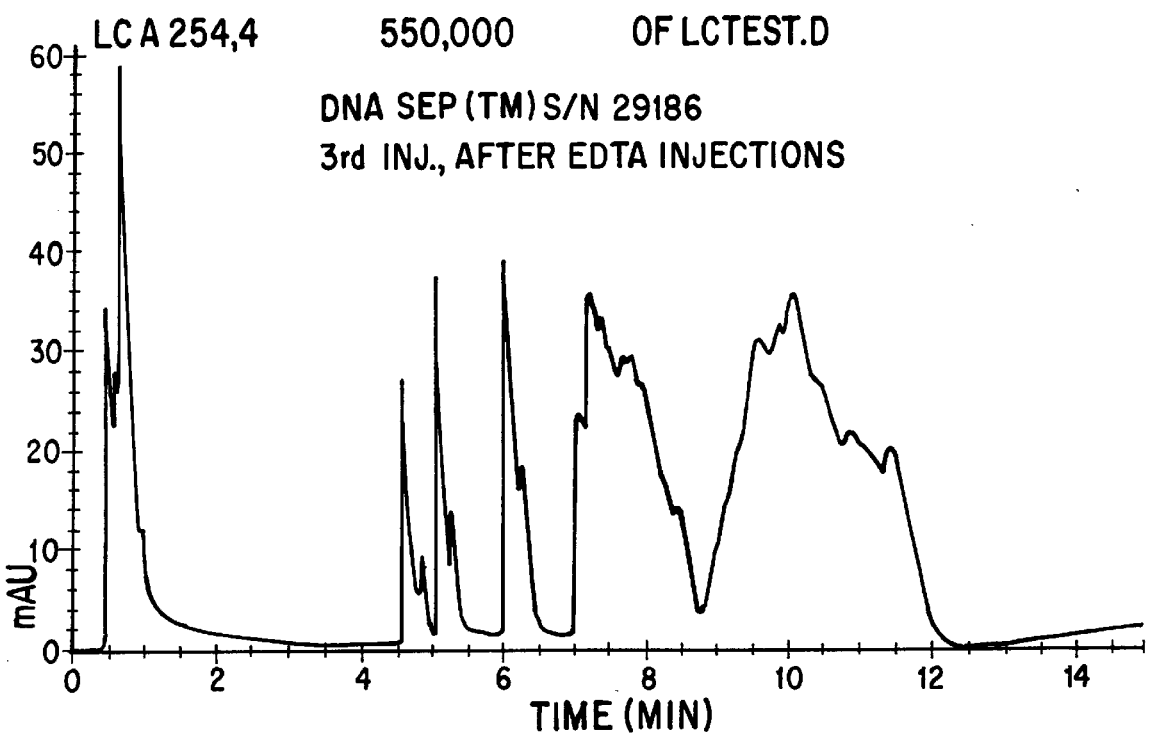
FIG. 2 shows further contamination and degradation of the HPLC separation now affecting all nucleic acid fragments down to 80 base pairs, with the larger fragments being affected the most.

The separation of a DNA standard resulted in inconsistent degrading performance, as shown in FIGS. 1 and 2. Then, 0.1 mM tetrasodium EDTA was added to eluants A and B. While this improved performance, degradation of the column still occurred after one day of use.

The instrument was then outfitted with a column containing 0.5 µm titanium frits and an iminodiacetate guard disk positioned in front of the column. This modification resulted in several days of separation with no degradation of performance.

Later, a guard cartridge with dimensions of 10×3.2 mm, containing iminodiacetate chelating resin of 2.5 mequiv/g capacity and 10 µm particle size was positioned directly in front of the injection valve. This also resulted in elimination of the contamination problem. The system was able to operate with or without the guard disk in this mode.

The minimum modifications needed to practice the invention to achieve improved nucleic acid separations involve using a stainless steel HPLC system that has been retrofitted with a chelating disk or cartridge positioned in front of the injection valve or column and a column containing titanium or PEEK frits.

While the use of tetrasodium EDTA by itself is not always adequate, its use does not degrade performance unless the concentration is high and the EDTA contributes to the driving ion action in the ion pairing separation, or if mass spectrometry detection is used, or if fractions are collected for subsequent analysis.

The performance of any column capable of separating DNA can be improved through the column protection methods and system described in this example. Other columns that have been used to separate double-stranded DNA include nonporous alkylated reverse phase silica materials, large pore poly(styrene/divinylbenzene) and other polymeric materials, and large pore silica-based reverse phase materials.

Example 6

The column material described in Example 5 is packed in column body hardware consisting of titanium, PEEK, or other polymeric material, and the column frits are titanium, PEEK, or other polymeric material. The HPLC system still requires minimum column protection, as described in Example 5, consisting of a chelating ion exchange resin positioned in front of the injection valve or in front of the column.

Example 7

The performance of the HPLC system can be improved by employing polymeric or titanium in all of the frits. In the case of a Hewlett-Packard HP1090 instrument, polymeric inlet eluant filters replaced the standard stainless steel filters. Titanium frits replaced the stainless steel frits used in the mixer after the pump head, but before the chelating ion exchange cartridge before the injector. This resulted in a several-week lifetime of the cartridges before breakthrough of contaminants could occur.

Example 8

Alternatively, a PEEK or titanium HPLC system can be employed for double-stranded nucleic acid separation. In this case, a column containing titanium frits or PEEK frits must be used. Column protection consisting of the chelating cartridge positioned before the injection valve and/or the guard disk positioned before the column is preferred, but not necessary. Eluant containing a chelating reagent is preferred, but not necessary, and is used only in cases where collection of the DNA is not required.

A Waters Action Analyzer was outfitted with a column, as described in Examples 1 and 2, containing 0.5 μm titanium frits. The HPLC instrument was a low-pressure quaternary gradient system that contained polymeric inlet filters and PEEK pump heads, frits, and tubing. The inlet and outlet check valves were also PEEK, except for a ceramic seat and sapphire ball. A Waters 484 detector was used, with the detection wavelength set to 254 nm.

In this example, all of the flow paths were either titanium, sapphire, ceramic, or PEEK, except for the column body, which was 316 stainless steel. The 316 stainless steel body was passivated with dilute nitric acid prior to packing of the chromatographic material. The 316 stainless steel column body was preferred for use in this example because titanium column bodies were not available with smooth inside walls, and PEEK column bodies flexed during the packing process, leading to less efficient column beds.

Obviously, numerous modifications and variations of the present invention are possible in light of the above teachings. It is therefore to be understood that within the scope of the appended claims, the invention may be practiced otherwise than as specifically described herein.

All references cited herein are hereby incorporated by reference in their entirety.

What is claimed is:

1. A method for improving separation of nucleic acid fragments into fractions based on their molecular weight during passage through a liquid chromatographic column containing a resin bed comprising IPRPC DNA separation particles, wherein the method comprises supplying and feeding solutions entering the column with components having process solution-contacting surfaces which contact process solutions held therein or flowing therethrough, wherein said process solution-contacting surfaces are material which does not release multivalent cations into aqueous solutions held therein or flowing therethrough, whereby the column is protected from multivalent cation contamination of the contents thereof, and wherein the nucleic acid fragments are separated by ion pairing reverse phase chromatography.

2. The method of claim 1, wherein said process solution-contacting surfaces are material selected from the group consisting of titanium, coated stainless steel, and organic polymer.

3. The method of claim 1, wherein said IPRPC DNA separation particles particles comprise alkylated non-porous polymer beads having an average diameter of about 1–100 microns.

4. The method of claim 1, wherein multivalent cations in eluant solutions and sample solutions entering the column are removed by contacting said solutions with multivalent cation capture resin before said solutions enter the column to protect the resin bed from multivalent cation contamination, wherein said multivalent capture resin is selected from cation exchange resin and chelating resin.

5. The method of claim 1, wherein the nucleic acid fragments are double-stranded.

6. The method of claim 5, wherein the nucleic acid fragments comprise 80 or more base pairs.

7. A method for improving separation of nucleic acid fragments into fractions based on their molecular weight during passage through a liquid chromatographic column containing a resin bed comprising IPRPC DNA separation particles, wherein multivalent cations in process solutions entering the column are removed by contacting said solutions with multivalent cation capture resin, selected from cation exchange resin and chelating resin, before said solutions enter the column to protect the resin bed from multivalent cation contamination, and wherein the nucleic acid fragments are separated by ion pairing reverse phase chromatography.

8. The method of claim 7, wherein said multivalent cation capture resin is cation exchange resin having an ion exchange moiety selected from the group consisting of iminodiacetate, nitriloacetate, acetylacetone, arsenazo, hydroxypyridinone, and 8-hydroxyquinoline groups.

9. The method of claim 8, wherein said ion exchange moiety is an iminodiacetate group.

10. The method of claim 7, wherein said multivalent cation capture resin is contained in a guard disk, guard column, or guard cartridge.

11. The method of claim 7, wherein said IPRPC DNA separation particles comprise alkylated non-porous polymer beads having an average diameter of about 1–100 microns.

12. The method of claim 7, wherein the method further comprises supplying and feeding solutions entering the column with components having process solution-contacting surfaces which contact process solutions held therein or flowing therethrough, wherein said process solution-contacting surfaces are material which does not release multivalent cations into process solutions held therein or flowing therethrough, whereby the column is protected from multivalent cation contamination of the contents thereof.

13. The method of claim 12, wherein said process solution-contacting surfaces are material selected from the group consisting of titanium, coated stainless steel, and organic polymer.

14. The method of claim 7, wherein the nucleic acid fragments are double-stranded.

15. The method of claim 14, wherein the nucleic acid fragments comprise 80 or more base pairs.

* * * * *